(12) United States Patent
Zhang (10) Patent No.: US 9,796,960 B2
(45) Date of Patent: Oct. 24, 2017

(54) METHOD FOR PREPARING AND USING CELL GHOST WITH ACTIVE FACTORS AS SYNERGIST OF LYMPHOCYTE IN VITRO CULTURE

(71) Applicant: Mingjie Zhang, Shenzhen (CN)

(72) Inventor: Mingjie Zhang, Shenzhen (CN)

(*) Notice: Subject to any disclaimer, the term of this patent is extended or adjusted under 35 U.S.C. 154(b) by 0 days.

(21) Appl. No.: 15/106,985

(22) PCT Filed: Jan. 13, 2014

(86) PCT No.: PCT/CN2014/070545
§ 371 (c)(1),
(2) Date: Jun. 21, 2016

(87) PCT Pub. No.: WO2015/103793
PCT Pub. Date: Jul. 16, 2015

(65) Prior Publication Data
US 2017/0037371 A1    Feb. 9, 2017

(51) Int. Cl.
*C12N 5/078* (2010.01)
*C12N 5/0783* (2010.01)
*A61K 35/17* (2015.01)

(52) U.S. Cl.
CPC ............ *C12N 5/0638* (2013.01); *A61K 35/17* (2013.01); *C12N 5/0637* (2013.01); *C12N 5/0646* (2013.01); *C12N 2501/20* (2013.01); *C12N 2501/2302* (2013.01); *C12N 2501/2315* (2013.01); *C12N 2501/2321* (2013.01); *C12N 2501/50* (2013.01); *C12N 2501/51* (2013.01); *C12N 2502/11* (2013.01); *C12N 2502/1114* (2013.01); *C12N 2502/1164* (2013.01); *C12N 2502/99* (2013.01)

(58) Field of Classification Search
CPC .................................................... C12N 5/0634
See application file for complete search history.

(56) References Cited

U.S. PATENT DOCUMENTS

2010/0092516 A1*   4/2010   Lubitz ............... A61K 39/0258
                                                        424/234.1

OTHER PUBLICATIONS

Ryu et al., "Zinc transporters ZnT1 (Slc30a1), Zip8 (Slc39a8), and Zip10 (Slc39a10) in mouse red blood cells are differentially regulated during erythroid development and by dietary zinc deficiency," J Nutrition, Biochemical, Molecular, and Genetic Mechanisms, 138:2076-2083, 2008.*

\* cited by examiner

*Primary Examiner* — Rosanne Kosson
(74) *Attorney, Agent, or Firm* — Lathrop Gage LLP (57) ABSTRACT

Provided is a method for preparing and using cell ghosts with active factors as a synergist of a lymphocyte in vitro culture. The method for preparing cell ghosts comprises: washing a cell to obtain a washed cell; and cleaving the washed cell to obtain cell ghosts, wherein the cell has cytokines capable of promoting the proliferation and differentiation of lymphocytes on their surface.

14 Claims, 8 Drawing Sheets

METHOD FOR PREPARING AND USING CELL GHOST WITH ACTIVE FACTORS AS SYNERGIST OF LYMPHOCYTE IN VITRO CULTURE

FIELD

The present disclosure relates to the field of cell biology, particularly to a method for culturing lymphocytes with cell ghosts bearing active cytokines as an in vitro booster and use thereof, more particularly to a method for culturing lymphocytes with cell ghosts bearing active cytokines as an in vitro booster and use thereof in amplifying and activating lymphocytes.

BACKGROUND

The in vitro proliferation and differentiation of lymphocytes are regulated by many factors. The most common regulators mainly are soluble cytokines, various natural cells, and genetically engineered recombinant cells. In vitro cell culture, regulation mediated by the genetically engineered recombinant cells expressing a certain cytokines as feeder cells or antigen-presenting cells (APCs) on lymphocytes is often stronger than that by free cytokines, indicating advantage of immobilized cytokines. Therefore, the genetically engineered recombinant cells expressing certain cytokines are commonly used as the feeder cells or APCs to promote the proliferation and activation of lymphocytes. Both the feeder cells and the APCs are auxiliary cells; therefore it is necessary to deactivate their proliferative activity in order to not affect the in vitro proliferation and activation of lymphocytes. The commonly used methods include gamma ray irradiation, UV irradiation, physical methods such as electric shock and chemical treatments such as mitomycin. But there are still many defects, such as inability of large-scale preparation, expensive equipment, unsafe operation, being hard to control the degree of inactivation, possible residual live cells, or utter destruction of cells, etc. In addition, both physical and chemical methods can lead to crosslinking or destruction of nucleic acids. Although the cross-linked or destructed nucleic acids no longer function in cell proliferation, they still remain in the cells as genetic materials and moreover these nucleic acids or even the debris of them may be integrated into other genes, which is a major obstacle for clinical application of the prepared cells.

Therefore, how to obtain an effective and safe in vitro booster of lymphocytes remains an outstanding challenge in biology.

SUMMARY

The present disclosure directs to solve at least one of the challenges existing in the prior art. For this purpose, an object of the present disclosure is to provide a method for preparing cell ghosts.

The present disclosure is achieved based on the following findings of inventors: inventors found that, direct contact between lymphocytes and feeder cells is necessary for lymphocyte amplification and activation stimulated by feeder cells, but the intracellular soluble components in the feeder cells are not essential. For example, K562-mIL15-41BB feeder cells used to stimulate amplification and activation of NK cells (natural killer) express a large amount of green fluorescent proteins (GFPs) with green fluorescence visible to the naked eye in dark background. The green color of cells becomes more obvious when K562-mIL15-41BB feeder cells are harvested and centrifuged to the bottom of a centrifuge tube before gamma ray treatment. The green color gradually fades away upon each round of PBS washing after the gamma ray treatment, suggesting cell membrane damage caused by gamma ray treatment. Although no systematic analysis of such phenomenon has been reported so far, it is obvious that a mass amount of cellular components have been removed in the process. Hence, the truly effective component in this process is cell membrane. Removal of other cellular components should not only have no impact on its function, but also make the amplification and activation of lymphocytes safer in clinical application. In other words, empty intact cell membrane of feeder cells or APCs (i.e. cell ghost) with all the intracellular components removed should also preserve the function of feeder cells or APCs.

Therefore, in one aspect of present disclosure, a method for preparing cell ghosts is provided. According to embodiments of present disclosure, the method includes: washing cells to obtain washed cells; and lysing the washed cells to obtain the cell ghost, wherein cytokines capable of promoting lymphocytes proliferation and differentiation expressed on a cell surface. The inventors find that the method according to embodiments of the present disclosure allows rapid and effective preparation of the cell ghosts with simple and easily controlled operation, and is suitable for large-scale production.

It should be noted that cytokines on the cell surface capable of promoting lymphocytes to proliferate may be cytokines naturally expressed on the cell surface, or can be expressed on the cell surface through genetic engineering approaches (e.g. transient transfection or stable expression), or can also be the cytokines adsorbed or cross-linked onto the cell surface. In addition, the cells can be primary cells (e.g., peripheral blood mononuclear cells), or also can be cell lines (e.g., K562 cells).

According to embodiments of present disclosure, washing the cells further includes: suspending the cells in an isotonic solution to obtain cell suspension; and centrifuging the cell suspension to obtain the washed cells.

According to embodiments of present disclosure, prior to suspending the cells in the isotonic solution, the isotonic solution is cooled to 4° C. in advance.

According to embodiments of present disclosure, the isotonic solution is an isotonic phosphate buffer (PBS) at pH 7.4.

According to embodiments of present disclosure, lysing the washed cells further includes: suspending the washed cells in a hypotonic solution at a predetermined volume ratio followed by still standing for 2 hours, to obtain cell lysates; and centrifuging the cell lysates to obtain the cell ghost.

According to embodiments of present disclosure, the predetermination volume ratio is 1:40, thereby improving efficiency of cell lysis.

According to embodiments of present disclosure, prior to suspending the washed cells in the hypotonic solution, the hypotonic solution is cooled to 4° C. in advance.

According to embodiments of present disclosure, the hypotonic solution is a hypotonic Tris HCl buffer, thereby improving the efficiency of cell lysis.

According to embodiments of present disclosure, the cytokines capable of promoting lymphocytes proliferation and activation are at least one selected from a group consisting of IL-4, IL-7, IL-15, IL-21, CD19, CD64, CD86, and 4-1BBL.

In one embodiment of the present disclosure, cell ghosts are prepared by the following description. a) Reagents for preparing the cell ghost: 1) isotonic PBS: 0.15 mol/L NaCl, pH 7.4; 2) Hypotonic Tris HCl buffer: 10 mmol/L, pH 7.4. b) Operation steps: 1) collecting and washing cells: suspending cells in about 3-times volume of pre-cooled isotonic PBS solution; centrifuging at 600 g (1500 rpm) for 10 minutes at 4° C.; removing the supernatant and washing for 1 to 3 times. 2) lysing and washing cell membranes: adding pre-cooled 10 mmol/L hypotonic Tris HCl buffer into the washed cells at a ratio of 40:1 along with constant slow mixing, followed by stored at 4° C. for about 2 hours to allow complete lysis; centrifuging at 12000 g (9000 rpm) for 10 minutes at 4° C. to precipitate the cell membranes; washing and centrifuging repeatedly to obtain the cell ghost. 3) Aliquoting obtained cell ghosts at a concentration of about $2 \times 10^7$/ml, and storing at −80° C. in freezer medium, or at 4° C. after lyophilization.

In another aspect of present disclosure, the advantages of the cell ghosts are provided in embodiments. According to embodiments of present disclosure, the cell ghosts are prepared according to the method mentioned above. Inventors surprisingly found that the intact empty cell membrane (i.e. the ghost cell) can play the role of feeder cells or APCs. As compared with free cytokines, the feeding or antigen presenting function of the intact empty cell membrane expressing certain cytokines is stronger. The intact cell membrane shows comparable feeding and antigen presenting function as feeder cells or APC of prior art, and at the same time, demonstrates similar safety as free cytokines due to removal of nucleotides and other possible toxic intracellular components. The cell ghosts can also be prepared into different formulations as normal peptides or proteins, beneficial for preparation, storage, transportation and application.

In a third aspect of present disclosure, there is provided a method for culturing lymphocytes, including: mixing lymphocytes with a liquid medium to obtain lymphocyte suspension; adding the lymphocyte suspension and the cell ghosts described above into a culture container; and culturing the lymphocyte and the cell ghosts in an incubator with saturated humidity and 5% $CO_2$ at 37° C. Therefore, large scale in vitro proliferation of lymphocytes is achieved, allowing production of large amount of lymphocytes within a short time period, and the obtained lymphocytes still have relatively strong immunization function. In addition, the cell ghosts added into the culture container can effectively play feeding and antigen presenting function, and at the same time showing safety equal to free cytokines due to removal of nucleotide and other possible intracellular toxic components.

According to embodiments of present disclosure, the lymphocytes include NK cells, CTL cells and Treg cells.

It should be further noted that the cell ghosts used in NK cell culture shall bear but not limited to any one of IL-15, IL-21, CD19, CD64, CD86, 4-1BBL and combinations thereof; the cell ghosts used in CTL cell culture shall bear but not limited to any one of IL-4, IL-7, 4-1BBL, combinations thereof and a CTL-specific antigen (including proteins, peptides, polysaccharides, etc.); the cell ghosts used in Treg cell culture bear but not limited to any one of CD64, and CD86 combinations thereof.

According to embodiments of present disclosure, the suspension includes 40 ml of the liquid medium and $5 \times 10^6$ lymphocytes. The ratio between the cell ghosts and the lymphocytes is 1:1, which is beneficial for the proliferation and growth of lymphocytes.

The technical solution according to embodiments of the present disclosure, a simple and effective method of using the cell ghosts bearing active cytokines (i.e. the cell ghosts of the present disclosure) to play the function of feeder cells or APCs is provided, such that multiple obstacles for the clinical application of lymphocytes obtained using the feeder cells as a booster for culturing lymphocytes has been solved. Meanwhile, inventors find that the method for preparing the cell ghosts provided in embodiments of the present disclosure can effectively prepare the cell ghost. Such the method is simple and easily controlled, allowing large-scale production and thus providing a safer, more effective and cost-effective clinical reagent that overcomes many shortcomings of prior art using gamma irradiation, UV irradiation, electroporation and antimitotic treatment to prepare the feeder cells or APCs. Most of the previous methods for preparing the feeder cells or APCs over-focused on unnecessary components. Both physical and chemical methods cause crosslinking or damage of nucleic acids or damage of cell membrane. Although the treated nucleic acids can no longer function in cell proliferation, they still remain in the cells as genetic materials and moreover these nucleic acids or even the debris may be integrated into the genes of limphocytes in culture.

In a fourth aspect of the present disclosure, a method for amplifying and activating lymphocytes is provided, including: isolating monocytes from human periphery blood; mixing the monocytes with 40 ml of a medium for lymphocytes to obtain lymphocyte suspension, wherein the complete culture medium for lymphocytes contains a RPMI 1640 medium supplemented with 200 IU/ml IL-2, 1 volume % of autologous plasma and 80 U/ml gentamicin, and 40 ml of the lymphocyte suspension contains $5 \times 10^6$ of the monocytes; adding the lymphocyte suspension and $5 \times 10^6$ of the cell ghosts described above into a T175 culture flask, and culturing in an incubator with saturated humidity and 5% $CO_2$ at 37° C.; adding another 40 ml of the RPMI1640 medium on Day 4; transferring cells in the T175 culture flask into a culture bag, adding the RPMI1640 medium up to 400 ml, and adding $8 \times 10^7$ the cell ghosts described above; passaging a culture product into two culture bags each containing 640 ml of the complete culture medium on Day 10; and collecting the culture product to obtain the lymphocytes on Day 12, wherein, the lymphocytes include NK cells, CTL cells and Treg cells. Inventors surprisingly find that the method described herein can quickly and effectively amplify lymphocytes. In addition, the above mentioned the cell ghosts added during culture can effectively stimulate lymphocyte proliferation, without residual DNA and toxic components due to removal of intracellular nucleic acid and other possible toxic and harmful ingredients, as a result the amplified cells can be used in clinical applications.

The present disclosure demonstrates a stronger activity of the cytokines on the cell ghosts. As compared with nanoparticle preparation, using the cell ghosts as feeder cells or APC is better. This is because the inorganic nanoparticles are more or less incompatible with cultured cells or organisms; on the other hand, when using cell lines to prepare the cell ghost, antigens associated with certain cancer on the cell membrane are more conducive to induce more effective cytotoxic T lymphocytes (CTL) towards certain cancer. Illustration to preparation of CTL and Treg are made herein by taking a booster for in vitro culturing NK cells as an example, along with detailed description to its use.

In order to more clearly illustrate the significance of the present disclosure, a method preparing the feeder cells by gamma ray irradiation is taken as a control in the embodiments of present disclosure. The specific method includes: suspending the feeder cells in pH 7.4 isotonic PBS at a concentration of $1 \times 10^7$/mL; exposing the feeder cells to 10,000 unit of radiation; washing the feeder cells with pH=7.4 isotonic PBS solution for 3 times; suspending the feeder cell in fluid medium and adjusting the feeder cells to a concentration of $2 \times 10^7$/ml. It can be used freshly or can be stored at $-80°$ C. in freeze medium.

To more clearly illustrate the advantages of the present disclosure, there is provided in embodiments a method for detecting DNA or RNA in the feeder cells and the cell ghost for comparison, including: extracting total DNA followed by quantification via a diphenylamine reaction; extracting total RNA via Guanidine thiocyanate combined with phenol-chloroform method followed by quantification via an orcinol reaction. The cell ghosts according to embodiments of the present disclosure are tested to be negative for DNA or RNA. This indicates that all nucleic acids in the cells can be removed using the method provided in embodiments of the present disclosure, which will not be further explained in the following embodiments.

Inventors have found that the cell ghosts with active cytokines can effectively stimulate in vitro amplification and activation of lymphocytes and the obtained lymphocytes have good immune response. The lymphocytes mentioned in embodiments of the present disclosure originate from peripheral mononuclear cells (PBMC). The method for amplifying and activating NK cells are taken as embodiments. It would be appreciated by those skilled in the art that CTL and Treg cells may be amplified and via a similar method using corresponding cell ghosts (the feeder cells) or APCs. The method includes the following steps:

1) preparing autologous plasma: collecting 50 ml peripheral blood with anticoagulant added, followed by centrifugation (700 g) for 20 min at room temperature; extracting plasma and placing in a water bath at $56°$ C. for 30 min, standing at $4°$ C. for 15 min; centrifuging (900 g) at $4°$ C. for 30 min; and preserving the autologous plasma at $4°$ C.;

2) adding D-PBS into a cell layer after plasma collection followed by well mixing; separating PBMC by overlaying onto lymphocyte separation solution and centrifugation at 800 g for 20 min;

3) transferring obtained PBMC into a T175 culture flask, adding 40 ml of the complete culture medium for culturing the lymphocytes (RPMI 1640 supplemented with approximately 200 IU/ml IL-2, 1-10% autologous plasma (v/v), and 80 U/ml gentamicin) to prepare cell suspension (about $5 \times 10^6$ lymphocytes); adding $5 \times 10^6$ feeder cells or the cell ghosts, and culturing in an incubators at $37°$ C., saturated humidity and 5% $CO_2$;

4) adding another 40 mL of the complete culture medium for culturing the lymphocytes around Day 4;

5) transferring cells in the T175 culture flask to a culture bag, and adding about 400 ml of the medium for culturing the lymphocytes and about $8 \times 10^7$ cell ghosts mentioned previous around Day 7;

6) passaging cultures in the culture bag to two culture bags each containing about 640 ml of the complete culture medium for culturing the lymphocytes around Day 10;

7) collecting a culture product to obtain NK cells around Day 12, (or if more NK cells are needed, adding the complete culture medium to 1280 ml/bag); 8) transferring to two culture bags, and adding the full medium for culturing the lymphocytes up to about 850 ml/bag around Day 12, 9) taking about 500 ml of cell suspension from each bag with a total of about 1000 ml of cell suspension from the two culture bags, collecting cells and transfusing back to a patient and adding about 150 ml/bag of fresh full medium for culturing the lymphocytes around Day 16;

10) collecting cells from remaining cell suspension (approximately 1000 ml), and transfusing obtained cells back to a patient around Day 18. It would be appreciated by those skilled in the art that the NK cells may be cultured for different time periods based on desired amount of NK cells.

In order to better demonstrate that the NK cells prepared with the cell ghosts bearing the active cytokines have stronger ability to kill tumor cells as compared with those prepared by other existing methods, the present disclosure provides in embodiments a method for detecting cytotoxicity, specifically including the following steps:

1) thawing a tube of effector cells such as NK cells, on the day before measurement, and culturing thawed cells with a RPMI 1640 full medium supplemented with 10% fetal bovine serum and 80 U/ml gentamicin;

2) using one cell line as target cells for each analysis, requiring $6 \times 10^5$ effector cells and $3 \times 10^5$ target cells;

3) diluting Calcein-AM with the complete RPMI 1640 medium to prepare a CAM solution;

4) suspending $10^6$ target cells in 1 mL of CAM solution; culturing at $37°$ C. for 1 hour with timely shaking; washing twice with the complete RPMI 1640 medium, followed by centrifugation at 1200 rpm for 5 min each time; counting the number of cells and adjusting a concentration to be $1 \times 10^5$/ml;

5) diluting the effector cells to a concentration of $1 \times 10^6$/ml and seeding on the 96-well plate with U-shaped bottom with triplicates, and adding 200 µl target cells per well, thus resulting in a ratio of effector cells to target cells (E:T) of 10:1;

6) adding 100 µl 2% Triton X-100 into a well with maximum release, and adding 100 µl the complete RPMI 1640 medium into other wells.

7) diluting the effector cells in series by 5 times, by which the well with the last dilution has a ratio of the effector cells to the target cells (E:T) of 0.3125:1;

8) adding 100 µl target cells into each well, centrifuging at 100 g for 1 min to direct cells to contact, and culturing in an incubator for 4 hours with $37°$ C. and 5% $CO_2$;

9) pipetting the cells with a 100 µl pipette gently to suspend released calcein; precipitating cells by centrifugation at 100 g for 5 min; transferring 100 µl supernatant to a new culture plate, avoiding bubbles being formed. The bubbles, if there exist, should be punctured with a needle;

10) reading the plate using a fluorescence plate reader (excitation light at 485 nm, emission light at 530 nm); and 11) calculating a percentage of specific cytotoxicity (testing group-natural releasing group)/(maximum release group-natural releasing group)×100.

DETAILED DESCRIPTION

The present disclosure provides a method of preparing cell ghosts bearing active cytokines as a booster for culturing lymphocytes in vitro and use thereof. Reference will be made in detail to embodiments of the present disclosure. The embodiments are explanatory, illustrative, and used to generally understand the present disclosure. The embodiments shall not be construed to limit the present disclosure. Specific techniques or conditions that are not indicated in the embodiments shall be in accordance with techniques or conditions as described in literatures of the present field or product specifications. The reagents and instruments without specified manufacturers are conventional products that can be purchased.

Embodiment 1

1. Preparation of RPMI 8866-Cell Ghost

In accordance with the following steps, cell ghosts were prepared using a cell line, RPMI 8866, in which the PRMI 8866 is human B lymphoblastoid cell line. The details are as follows:

The RPMI 8866 cells were suspended in 3-time volume of pH 7.4 isotonic PBS solution (pre-cooled to 4° C.), followed by centrifugation at 1500 rpm and 4° C. for 10 minutes. Remove the supernatant, and repeatedly washed 1-3 times to obtain the washed RPMI 8866 cells; then added the washed RPMI 8866 into 10 mmol/L hypotonic Tris HCl buffer solution (pre-cooled to 4° C.) at a volume ratio of 1:40, with slow stirring during addition. The obtained mixture was then put into 4° C. refrigerator for 2 hours to allow complete lysis of cells. Afterwards, the mixture was centrifuged at 9000 rpm, 4° C. for 10 minutes to precipitate the cell ghosts, followed by further repeated washing, and centrifugal precipitation for another 3-5 times to obtain RPMI 8866 cell ghosts, i.e. RPMI 8866-ghost. Then, aliquoted at a concentration of $2 \times 10^7$ cell ghosts/ml in freeze solution, and stored at −80° C.; or preserved at 4° C. after lyophilization.

2. Preparation of RPMI 8866-Gamma Feeder Cell

RPMI 8866-gamma feeder cells were prepared according to the following steps:

The RPMI 8866 cells were suspended in pH 7.4 isotonic PBS solution at a concentration of $1 \times 10^7$ cells/mL. The obtained cell suspension was subjected to 10 thousand rad gamma ray irradiation, and then washed with pH 7.4 isotonic PBS solution for three times to obtain the feeder cells, namely RPMI8866-gamma. The obtained feeder cells were then suspended in complete PRMI 1640 medium (supplemented with 10% fetal bovine serum, gentamycin 80 U/ml) at a concentration of $2 \times 10^7$ feeder cells/ml, and stored at −80° C. in freeze solution.

3. Amplification of NK Cells in PBMCs Using RPMI 8866-Ghost and RPMI 8866-Gamma Feeder Cells.

The NK cell proliferation in PBMCs was stimulated by RPMI 8866-ghost or RPMI 8866-gamma feeder cells. Peripheral blood mononuclear cells from 3 normal human subjects were tested as follows:

1) Preparation of autologous plasma: collecting 50 ml anticoagulant peripheral blood, followed by 700 g centrifugation for 20 min at room temperature; the plasma was collected and placed in 56° C. water bath for 30 min, then stood at 4° C. for another 15 min; lastly, the plasma was centrifuged again at 900 g, 4° C. for 30 min to obtain autologous plasma and stored at 4° C.

2) D-PBS was added into the cell layer after plasma extraction followed by well mixing. PBMCs were isolated with a lymphocyte separation solution via centrifugation at 800 g for 20 min;

3) Cell suspension (approximately $5 \times 10^6$ lymphocytes) was prepared by adding isolated PBMCs, 40 ml complete culture medium for culturing lymphocytes (RPMI 1640 supplemented with about 200 IU/ml IL-2, autologous plasma 1-10%, gentamicin 80 U/ml) and 1×10⁷ feeder cells or cell ghosts in a T175 culture flask, followed by incubating in an incubator with saturated humidity, 37° C., and 5.0% $CO_2$;

4) approximately 40 mL complete culture medium for culturing lymphocytes was added around Day 4;

5) All cells in the T175 culture flask were transferred into a culture bag followed by adding about 400 mL complete culture medium for culturing lymphocytes and adding about 8×10⁷ cell ghosts mentioned above around Day 7;

6) All cells in the culture bag were passaged to two new culture bags each containing about 640 mL complete culture medium for culturing lymphocytes around Day 10; and 7) collecting culturing products around Day 12, which were subjected to evaluation with amplification and activation on NK cells in PBSCs via different methods. The NK cells in PBSCs were cultured for different time period, such as for 18 to 20 continuous days, in accordance with the number of cells needed.

Figure 1:
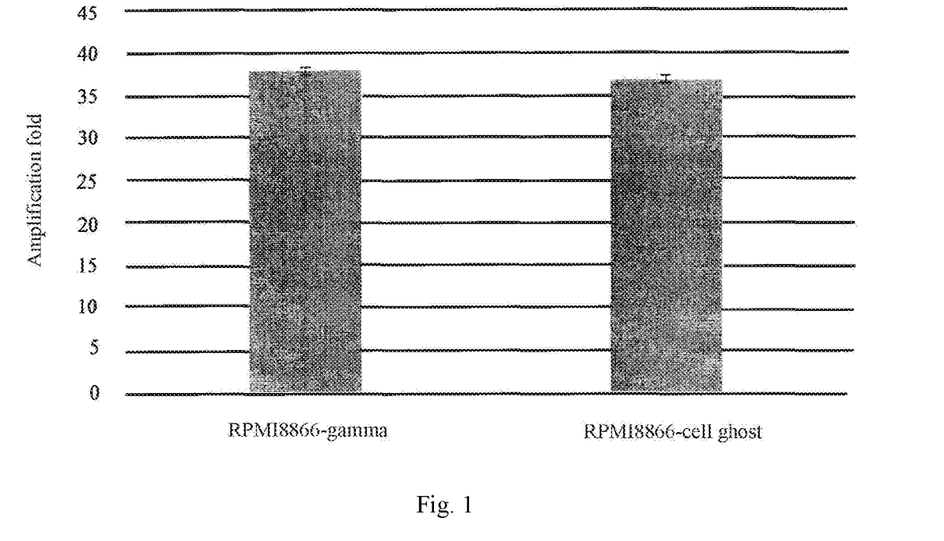
FIG. 1 is a graph showing comparison of in vitro amplification of NK cells in PBMCs stimulated by RPMI 8866-ghost and RPMI 8866-gamma, respectively, according to embodiment 1 of the present disclosure.

4. Comparison of In Vitro Amplification of NK Cells in PBMCs Stimulated by RPMI 8866-Gamma and RPMI 8866-Ghost Comparison of in vitro amplification of NK cells in PBMCs stimulated by RPMI 8866-ghost and RPMI 8866-gamma respectively was shown in FIG. 1. It indicates that the amplification effects of the NK cells respectively by the cell ghosts of the present disclosure and the feeder cells are comparable.

5. Comparison of Cytotoxicity of NK Cells in PBMCs Amplified and Activated by RPMI 8866-Gamma and RPMI 8866-Ghost Against Tumor Cells The NK cells obtained through in vitro amplification described above were taken as effector cells, and K562 leukemia cells (K562 cells) were taken as target cells. The cytotoxicity on K562 target cells after NK cells in PBMCs were stimulated and amplified by RPMI 8866-gamma and RPMI 8866-ghost were determined by Calcein-AM fluorescence scanning assay. Specific steps are as follows:

A CAM solution was prepared by diluting fluorescent dye Calcein-AM with the complete culture medium (RPMI1640 supplemented with 10% fetal bovine serum, 80 U/ml gentamicin). 1×10⁶ target cells were suspended in 1 ml of the CAM solution, and incubated in an incubator with saturated humidity, 37° C., and 5.0% $CO_2$ for one hour, with timely shaking during the culture. Then the target cells in culture were washed twice with NKEM medium, with 1200 rpm centrifugation for 5 minutes after every wash. The target cells were then counted for and then adjusted to be a concentration of 1×10⁵ cells/mL. The effector cells were diluted to be a concentration of 1×10⁶ cells/mL.

The target cells were added into 3 wells of a U-shaped bottom 96-well cell culture plate each containing 200 µL, corresponding to a ratio of effector cells to target cells (E:T) of 10:1. One of such three wells was added with 100 µL of 2% Triton X-100 such that the target cells were lysed completely to be as a positive control with maximum release. Other two wells were added with 100 µL of the complete culture medium to be as a negative control for natural release.

The effector cells were double-diluted 5 times, with a ratio of the effector cells to the target cells (E:T) of 0.3125:1 in the last dilution.

The number of sample wells on the 96-well plate is determined according to the total number of samples with different concentrations of effector cells, with 100 µl target cells added in each well and centrifuged at 100 g for 1 min to induce cell attachment. After cultured in the incubator with saturated humidity, 37° C. and 5.0% $CO_2$ for 4 hours, cells were gently pipetted up-and-down with a 100 µl pipette to suspend released Calcein fluorescence dye, followed by 5 min centrifugation at 100 g to precipitate cells. 100 µL supernatant was transferred to a new culture plate to be measured with a fluorescence plate-reader (excitation light at 485 nm, emission light at 530 nm). The cytotoxicity of NK cells in PBMCs after stimulated and amplified by RPMI 8866-gamma and RPMI 8866-ghost, respectively, on k562 cells, which is calculated in accordance with a formula of: killer rate=[(absorbance of the test group−absorbance of the natural release group)/(absorbance of the maximum release group−absorbance of the natural release group)]×100. Results are shown in FIG. 2.

Figure 2:
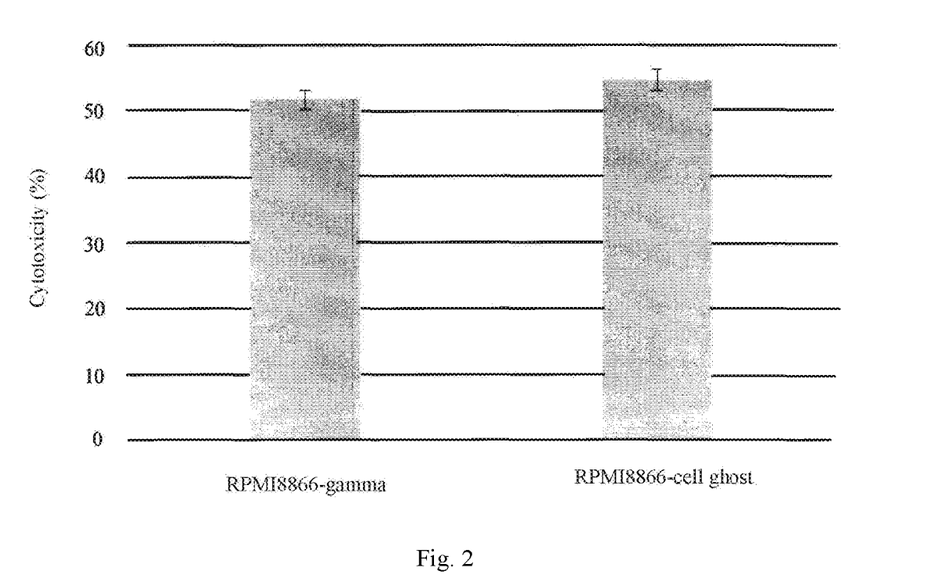
FIG. 2 is a graph showing comparison of cytotoxicity on K562 target cells after NK cells in PBMCs are stimulated and amplified by RPMI 8866-gamma and RPMI 8866-ghost, respectively, according to embodiment 1 of the present disclosure.

As shown in FIG. 2, NK cells in PBMCs exhibits strong toxicity on K562 cells after amplified and stimulated by RPMI8866-gamma and RPMI8866-ghost.

Embodiment 2

HFWT-gamma and HFWT-ghost were prepared with a cell line, HFWT cells (HFWT Wilms tumor cell line), respectively; and experiments on amplification and cytotoxicity of NK cells were performed via methods the same as above description in Embodiment 1.

Figure 3:
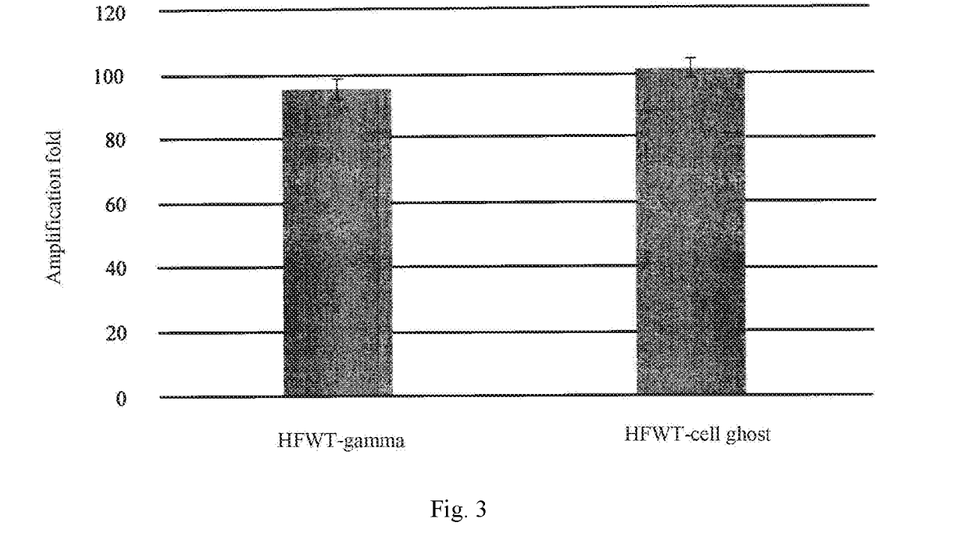
FIG. 3 is a graph showing comparison of in vitro amplification of NK cells in PBMCs stimulated by HFWT-gamma and HFWT-ghost, respectively, according to embodiment 2 of the present disclosure.

Comparison of in vitro amplification of NK cells in PBMCs stimulated by HFWT-gamma and HFWT-ghost, respectively is shown in FIG. 3. It can be seen that the NK cells are amplified by about 100 times averagely either by HFWT-gamma and HFWT-ghost on Day 12, indicating that the amplification of the NK cells respectively by the cell ghosts of the present disclosure and the feeder cells are comparable.

Figure 4:
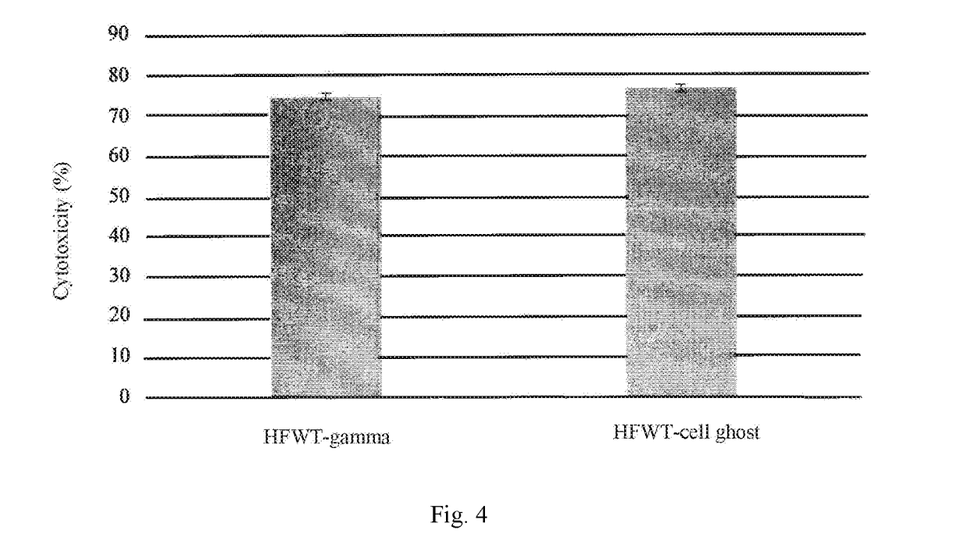
FIG. 4 is a graph showing comparison of cytotoxicity on K562 target cells after NK cells in PBMCs are stimulated and amplified by HFWT-gamma and HFWT-ghost, respectively, according to embodiment 2 of the present disclosure.

Cytotoxicity on K562 target cells after NK cells in PBMCs are stimulated and amplified by HFWT-gamma and HFWT-ghost are shown in FIG. 4. It can be seen that the NK cells in PBMCs after amplified and stimulated respectively by HFWT-gamma and HFWT-ghost exhibit strong toxicity on the K562 cells.

Embodiment 3

Figure 5:
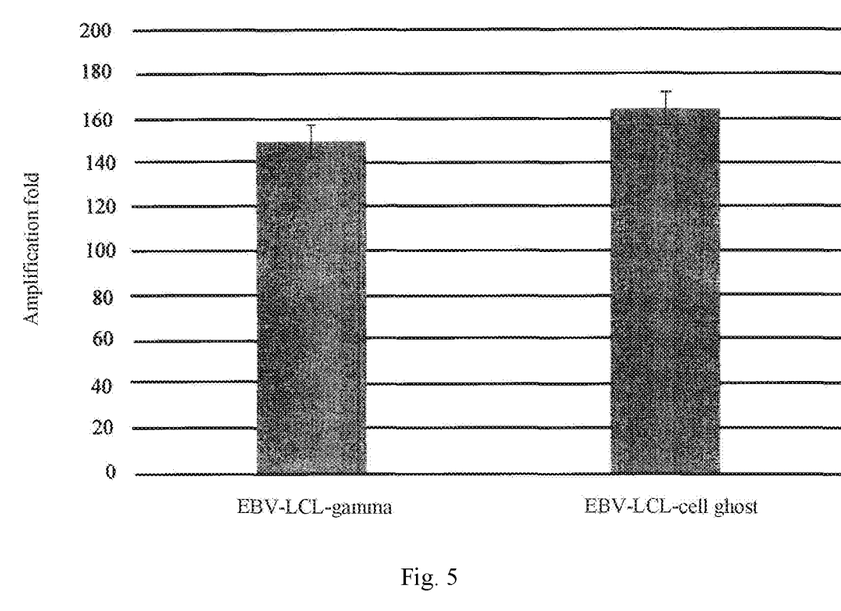
FIG. 5 is a graph showing comparison of in vitro amplification of NK cells in PBMCs stimulated by EBV-CLC-gamma and EBV-CLC-ghost, respectively, according to embodiment 3 of the present disclosure.

EBV-CLC-gamma feeder cells and EBV-CLC-ghost were prepared with EBV-CLC cells respectively, and experiments on amplification and cytotoxicity of NK cells were performed via methods the same as above description in Embodiment 1, in which EBV-CLC is a B lymphoblastoid cell line formed by EBV transformation of human B lymphocytes. The in vitro amplification of NK cells in PBMCs stimulated by EBV-CLC-gamma and EBV-CLC-ghost are shown in FIG. 5. It can be seen that average amplification rates by EBV-CLC-gamma and EBV-CLC-ghost are about 150 times on Day 12 respectively, indicating that the amplification of the NK cells by the cell ghosts of the present disclosure and the feeder cells are comparable.

Figure 6:
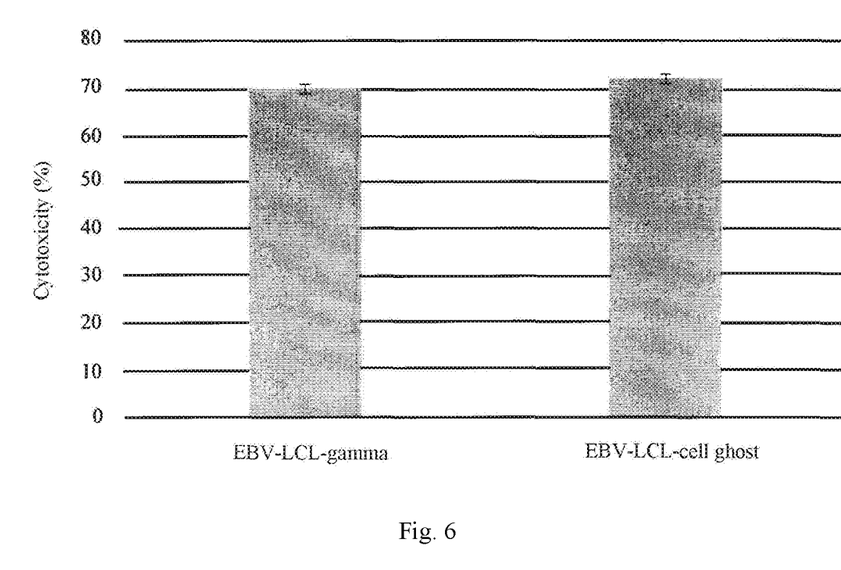
FIG. 6 is a graph showing comparison of cytotoxicity on K562 target cells after NK cells in PBMCs are stimulated and amplified by EBV-CLC-gamma and EBV-CLC-ghost, respectively, according to embodiment 3 of the present disclosure.

Cytotoxicity on K562 target cells after NK cells in PBMCs are stimulated and amplified by EBV-CLC-gamma and EBV-CLC-ghost are shown in FIG. 6. It can be seen that the NK cells in PBMCs after amplified and stimulated by EBV-CLC-gamma and EBV-CLC-ghost exhibit strong toxicity on the K562 cells.

Embodiment 4

K15-41BBL-gamma feeder cells and K15-41BBL-ghosts were prepared with a genetic recombinant cell line K15-

41BBL; and experiments on amplification and cytotoxicity of NK cells were performed via methods the same as above description in Embodiment 1, with a difference that the amplification of NK cells was detected on Day 20 during cell amplification process. K15-41BBL is a cell line prepared by expressing IL-15 and 4-1BBL on the surface of K562 cells.

Figure 7:
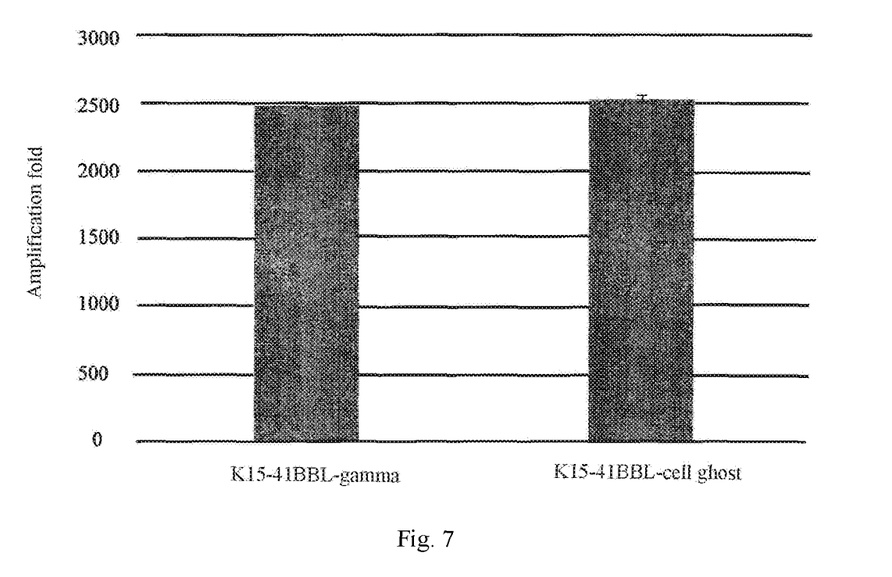
FIG. 7 is a graph showing comparison of in vitro amplification of NK cells in PBMCs stimulated by K15-41BBL-gamma and K15-41BBL-ghost, respectively, according to embodiment 4 of the present disclosure.

The in vitro amplification of the NK cells in PBMCs stimulated by K15-41BBL-gamma feeder cells and K15-41BBL-ghosts are shown in FIG. 7. It can be seen that average amplification rates by K15-41BBL-gamma feeder cells and K15-41BBL-ghosts are about 2500 times without significant differences on Day 20.

Figure 8:
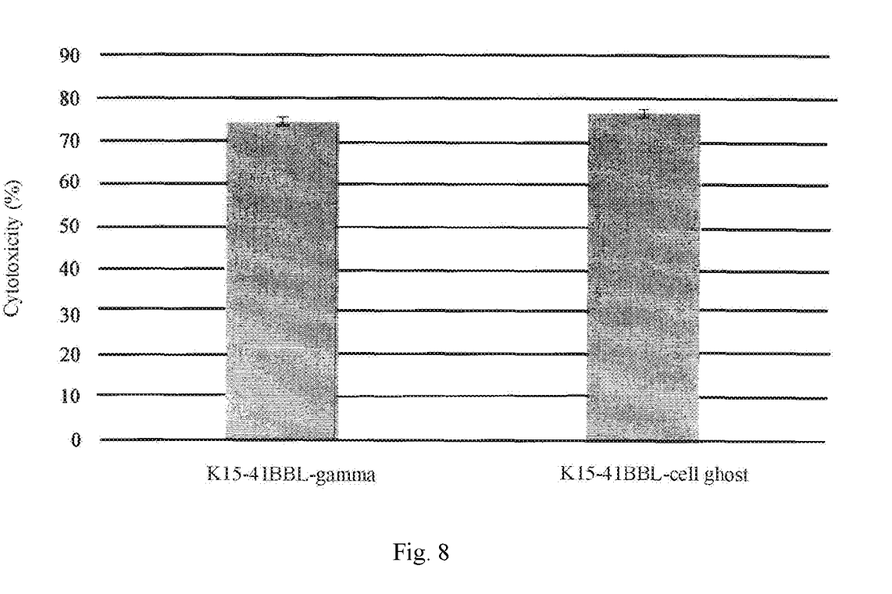
FIG. 8 is a graph showing comparison of cytotoxicity on K562 target cells after NK cells in PBMCs are stimulated and amplified by K15-41BBL-gamma and K15-41BBL-ghost, respectively, according to embodiment 4 of the present disclosure.

Cytotoxicity on K562 target cells after NK cells in PBMCs are stimulated and amplified by K15-41BBL-gamma feeder cells and K15-41BBL-ghosts are shown in FIG. 8. It can be seen that the NK cells in PBMCs after amplified and stimulated by K15-41BBL-gamma feeder cells and K15-41BBL-ghosts exhibit strong toxicity on the K562 cells without significant difference.

Embodiment 5

K21-41BBL-gamma feeder cells and K21-41BBL-ghosts were prepared with a genetic recombinant cell line K21-41BBL; and experiments on amplification and cytotoxicity of NK cells were performed via methods the same as above description in Embodiment 1, with a difference that the amplification of NK cells was detected on Day 20 during cell amplification process. K21-41BBL is a cell line prepared by expressing IL-21, IL-15, CD86, CD64, CD19, and 4-1BBL on the surface of K562 cells.

Figure 9:
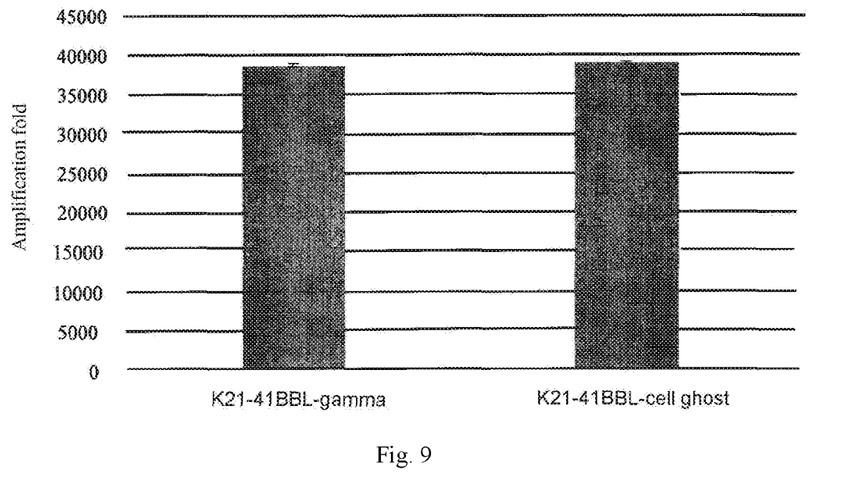
FIG. 9 is a graph showing comparison of in vitro amplification of NK cells in PBMCs stimulated by K21-41BBL-gamma and K21-41BBL-ghost, respectively, according to embodiment 5 of the present disclosure.

The in vitro amplification of the NK cells in PBMCs stimulated by K21-41BBL-gamma feeder cells and K21-41BBL-ghosts are shown in FIG. 9. It can be seen that average amplification rates by K21-41BBL-gamma feeder cells and K15-41BBL-ghosts are about 40,000 times without significant difference on Day 20.

Figure 10:
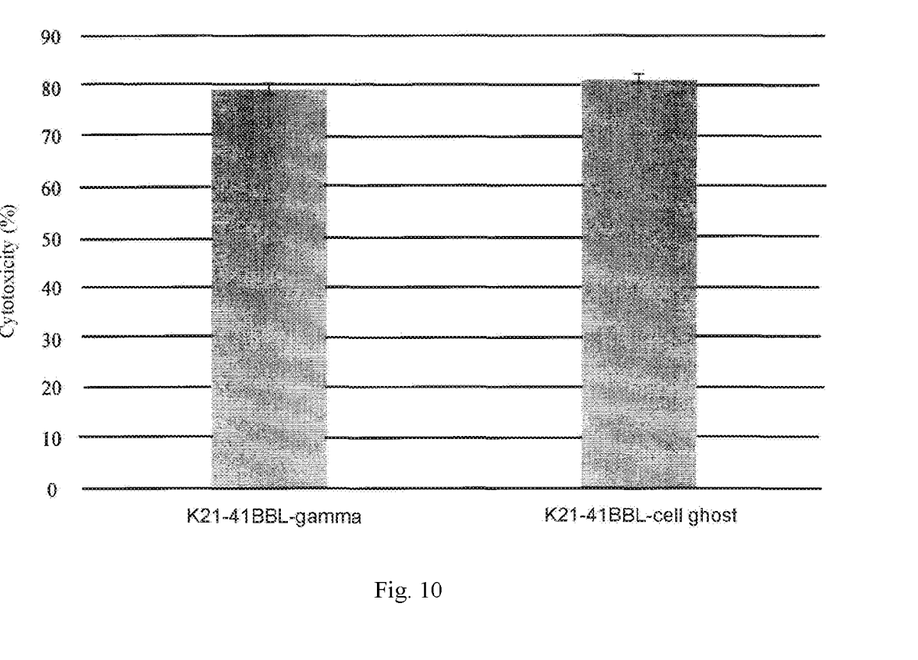
FIG. 10 is a graph showing comparison of cytotoxicity on K562 target cells after NK cells in PBMCs are stimulated and amplified by K21-41BBL-gamma and K21-41BBL-ghost, respectively, according to embodiment 5 of the present disclosure.

Cytotoxicity on K562 target cells after NK cells in PBMCs are stimulated and amplified by K21-41BBL-gamma feeder cells and K21-41BBL-ghosts are shown in FIG. 10. It can be seen that the NK cells in PBMCs after amplified and stimulated respectively by K21-41BBL-gamma feeder cells and K21-41BBL-ghosts exhibit strong toxicity on the K562 cells without significant difference.

Embodiment 6

TK21-41BBL-gamma feeder cells and TK21-41BBL-ghosts were prepared with a TK21-41BBL cell line, respectively; and experiments on amplification and cytotoxicity of NK cells were performed via methods the same as above description in Embodiment 1, with a difference that the amplification of NK cells was detected on Day 20 during cell amplification process. TK21-41BBL is a cell line prepared by transient transfecting with genes encoding IL-21, IL-15, CD64, CD19, CD86, and 4-1BBL proteins into K562 leukemia cells.

Figure 11:
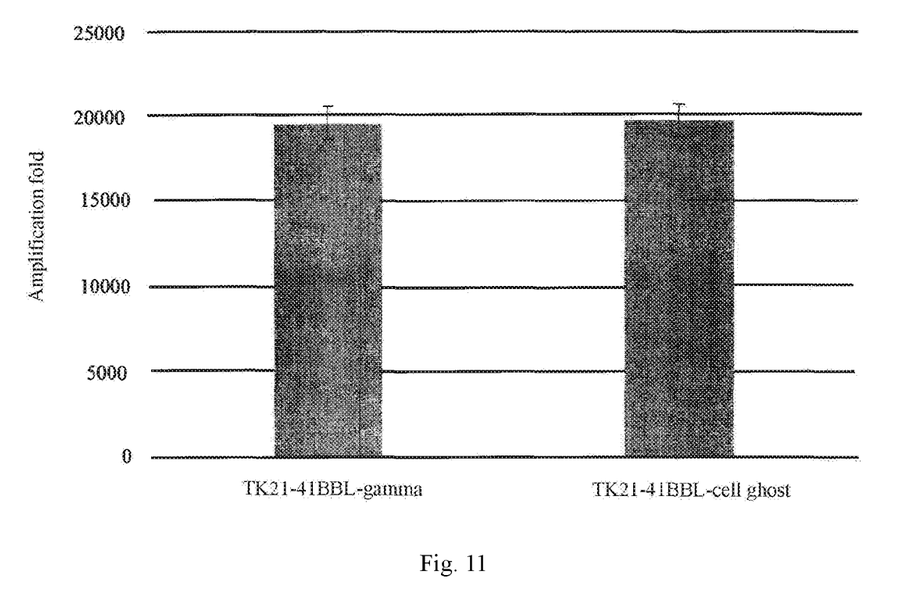
FIG. 11 is a graph showing comparison of in vitro amplification of NK cells in PBMCs stimulated by TK21-41BBL-gamma and TK21-41BBL-ghost, respectively, according to embodiment 6 of the present disclosure.

The in vitro amplification of the NK cells in PBMCs stimulated by TK21-41BBL-gamma feeder cells and TK21-41BBL-ghosts are shown in FIG. 11. It can be seen that average amplification rates by K21-41BBL-gamma feeder cells and K15-41BBL-ghosts are about 20,000 times without significant difference on Day 20.

Figure 12:
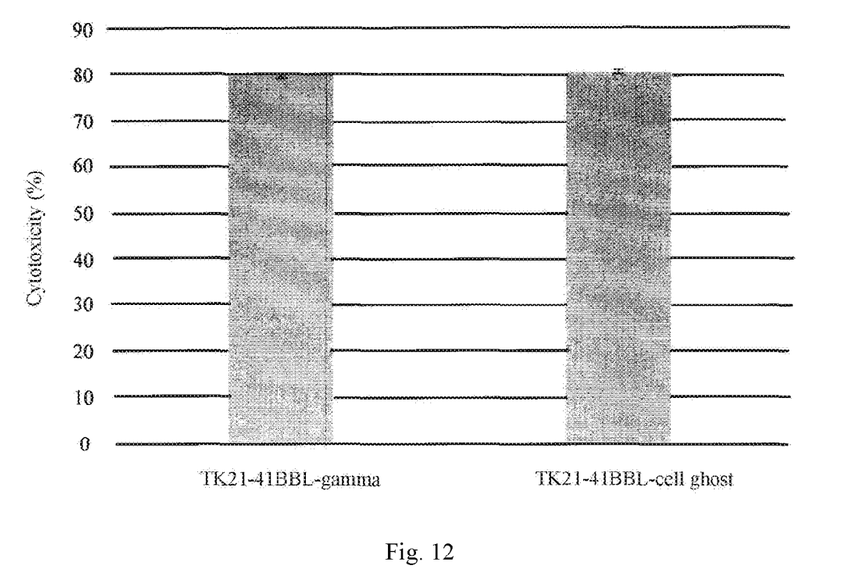
FIG. 12 is a graph showing comparison of cytotoxicity on K562 target cells after NK cells in PBMCs are stimulated and amplified by TK21-41BBL-gamma and TK21-41BBL-ghost, respectively, according to embodiment 6 of the present disclosure.

Cytotoxicity on K562 target cells after NK cells in PBMCs are stimulated and amplified by TK21-41BBL-gamma feeder cells and TK21-41BBL-ghosts are shown in FIG. 12. It can be seen that the NK cells in PBMCs after amplified and stimulated by TK21-41BBL-gamma feeder cells and TK21-41BBL-ghosts exhibit strong toxicity on the K562 cells without difference.

Embodiment 7

1. Preparation of Cells Ghost

Cells ghosts were prepared with K562 cells according to the method for preparing the cell ghosts in Embodiment 1, thereby obtaining K562-ghost. The K562-ghosts were cross-linked with a cytokine mixture of IL-21, IL-15, CD86, CD64, CD19 and 4-1BBL via a glutaraldehyde method, thereby obtaining PK21-41BBL-ghosts.

2. NK Cells Amplification

Figure 13:
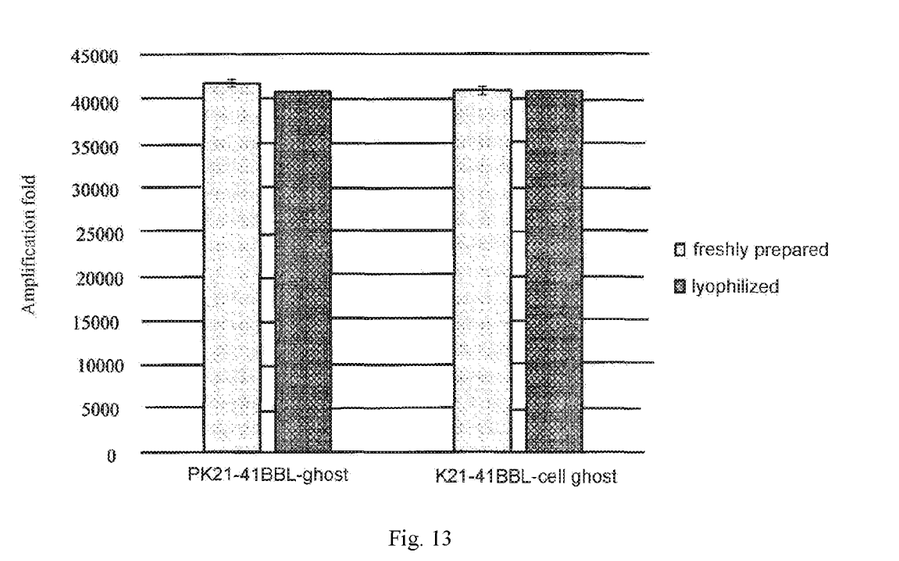
FIG. 13 is a graph showing comparison of in vitro amplification of NK cells in PBMCs stimulated by two formulations (fresh liquid and lyophilized) of PK21-41BBL-ghost and K21-41BBL-ghost, respectively, according to embodiment 7 of the present disclosure.

NK cells in PBMCs were stimulated and amplified respectively by two formulations (freshly prepared (directly obtained without preservation) and lyophilized (prepared, lyophilized and preserved in 4° C. refrigerator)) of the PK21-41BBL-ghosts and the K21-41BBL-ghost prepared in Embodiment 6 via methods the same as above description in Embodiment 1. The in vitro amplification of NK cells in PBMCs stimulated by the two formulations of K21-41BBL-ghosts and PK21-41BBL-ghosts, respectively, were detected in on Day 20, of which result is shown in FIG. 13. It can be seen that average amplification rates by PK21-41BBL-ghosts and K21-41BBL-ghosts are about 40,000 times without significant difference on Day 20.

3. Cytotoxicity Test

Figure 14:
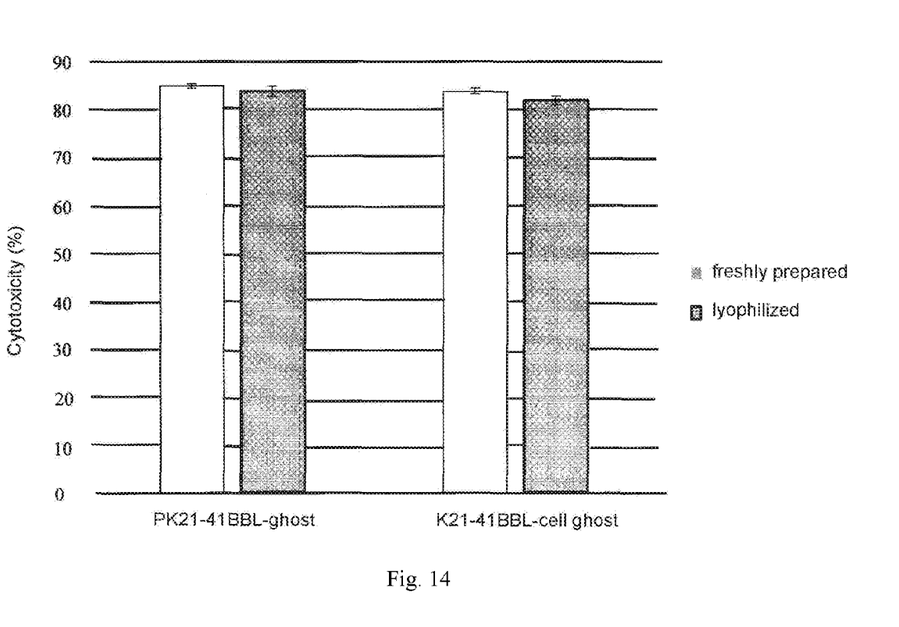
FIG. 14 is a graph showing comparison of cytotoxicity on K562 target cells after NK cells in PBMCs are stimulated and amplified by two formulations (fresh liquid and lyophilized) of PK21-41BBL-ghost and K21-41BBL-ghost, respectively, according to embodiment 7 of the present disclosure.

Cytotoxicity on K562 target cells after the effector NK cells in PBMCs are stimulated and amplified by two formulations (freshly prepared (directly obtained without preservation) and lyophilized (prepared, lyophilized and preserved in 4° C. refrigerator)) of K21-41BBL-ghosts and the PK21-41BBL-ghosts, respectively, are shown in FIG. 14. It can be seen that the NK cells in PBMCs after stimulated and amplified by the two formulations (freshly prepared and lyophilized) of PK21-41BBL-ghost and K21-41BBL-ghost exhibit strong cytotoxicity on the K562 cells.

Embodiment 8

1. Preparation of PBMC Ghosts, PBMC Ghosts Crosslinked with Cytokines, and PBMC Ghosts Attached with Cytokines PBMC-ghost was prepared with PBMCs via the method in Embodiment 1; the PBMC-ghosts were crosslinked with IL-21, IL-15, CD86, CD64, CD19 and 4-1BBL, thereby obtaining PBMC-ghost-cIL21-41BB.

Besides, PBMC-ghosts were mixed with soluble cytokines, such as IL-21, IL-15, CD86, CD64, CD19 and 4-1BBL, such that the cytokines were attached on the PBMC-ghost, i.e., PBMC-ghost-aIL21-41BB.

2. NK Cell Amplification

NK cells in allogeneic PBMCs (i.e., the PBMC used for preparing cell ghosts and feeder cells is different from the PBMC used for amplification) were stimulated and amplified by PBMC-ghost-cIL21-41BBL and PBMC-ghost-aIL21-41BBL mentioned above via the same method in Embodiment 1.

Figure 15:
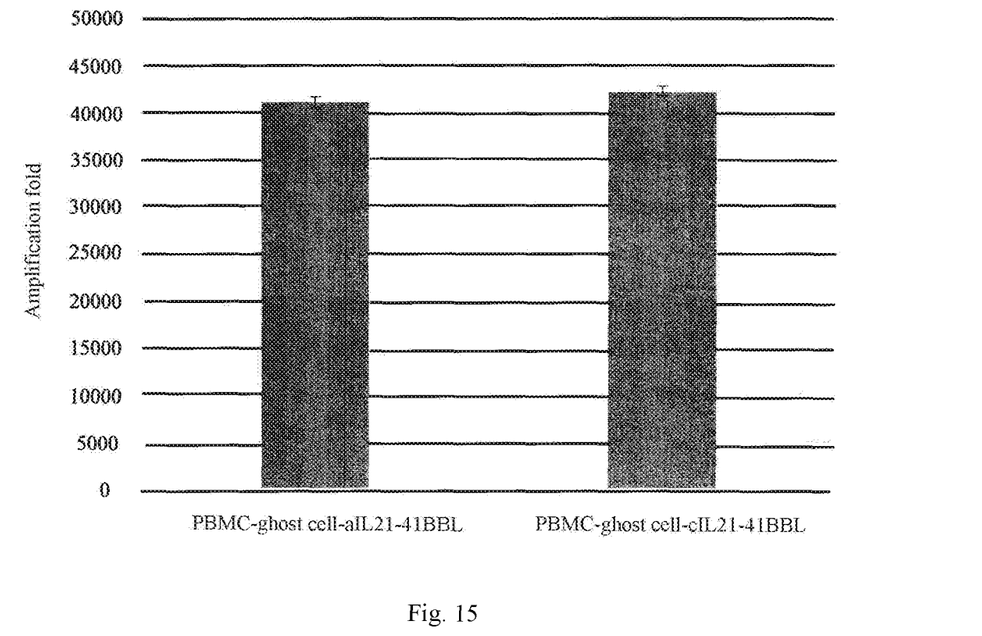
FIG. 15 is a graph showing comparison of in vitro amplification of NK cells in PBMCs stimulated by PBMC-ghost cIL21-41BBL and PBMC-ghost aIL21-41BBL, respectively, according to embodiment 8 of the present disclosure.

The in vitro amplification of NK cells in PBMCs stimulated by PBMC-ghost-cIL21-41BBL and PBMC-ghost-aIL21-41BBL were measured in on Day 20, of which result is shown in FIG. 15. It can be seen that average amplification rates by PBMC-ghost-cIL21-41BBL and PBMC-ghost-aIL21-41BBL are about 40,000 times without significant difference on Day 20.

3. Cytotoxicity Test

Figure 16:
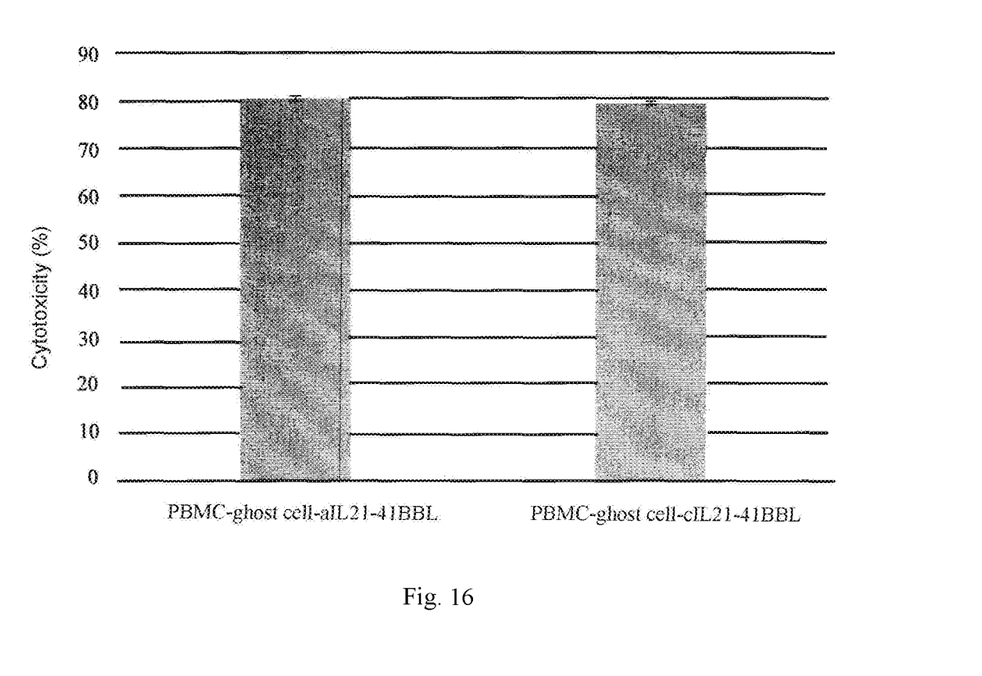
FIG. 16 is a graph showing comparison of cytotoxicity on K562 target cells after NK cells in PBMCs are stimulated and amplified by PBMC-ghost cIL21-41BBL and PBMC-ghost aIL21-41BBL, respectively, according to embodiment 8 of the present disclosure.

Cytotoxicity on K562 target cells after the effector NK cells in PBMCs are stimulated and amplified by PBMC-ghost-cIL21-41BBL and PBMC-ghost-aIL21-41BBL, respectively, are shown in FIG. 16. It can be seen that the NK cells in PBMCs after stimulated and amplified respectively by PBMC-ghost-cIL21-41BBL and PBMC-ghost-aIL21-41BBL exhibit strong cytotoxicity on the K562 cells without significant difference.

Reference throughout this specification to "an embodiment," "some embodiments," "one embodiment", "another example", "an example", "a specific examples", or "some examples", means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific examples", or "in some examples", in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for preparing cell ghosts, comprising:
    a) washing cells to obtain washed cells; and
    b) lysing the washed cells to obtain the cell ghosts, wherein said cells express on their surface cytokines capable of promoting lymphocyte proliferation and/or activation.

2. The method of claim 1, wherein washing the cells further comprises:
    a) suspending the cells in an isotonic solution to obtain a cell suspension; and
    b) centrifuging the cell suspension to obtain the washed cells.

3. The method of claim 2, wherein prior to suspending the cells in the isotonic solution, the isotonic solution is cooled to 4° C.

4. The method of claim 3, wherein the isotonic solution is an isotonic phosphate buffer at pH 7.4.

5. The method of claim 1, wherein lysing the washed cells further comprises:
    a) suspending the washed cells in a hypotonic solution at a predetermined volume ratio, followed by
    b) incubating the preparation of step (a) for 2 hours without mixing, to obtain cell lysates; and
    c) centrifuging the cell lysates to obtain the cell ghosts.

6. The method of claim 5, wherein the predetermined volume ratio of cells to total volume is 1:40.

7. The method of claim 5, wherein prior to suspending the washed cells in the hypotonic solution, the hypotonic solution is cooled to 4° C.

8. The method of claim 7, wherein the hypotonic solution is a hypotonic Tris HCl buffer.

9. The method of claim 1, wherein the cytokines capable of promoting lymphocyte proliferation and/or activation are at least one selected from the group consisting of IL-4, IL-7, IL-15, IL-21, CD19, CD64, CD86, and 4-1BBL.

10. The cell ghosts prepared according to the method of claim 1.

11. A method for culturing lymphocytes, comprising:
    a) mixing lymphocytes with a culture medium to obtain a lymphocyte suspension;
    b) adding the lymphocyte suspension and the cell ghosts of claim 10 into a culture container; and
    c) culturing the combination of the lymphocyte suspension and the cell ghosts obtained in step (b) in an incubator containing water-saturated air and 5% $CO_2$ at 37° C.

12. The method of claim 11, wherein the lymphocytes are at least one member selected from the group consisting of NK cells, CTL cells and Treg cells.

13. The method of claim 12, wherein the lymphocyte suspension has a volume of 40 ml and comprises $5\times10^6$ of the lymphocytes, and the ratio of the cell ghosts to the lymphocytes is 1:1.

14. A method for amplifying and/or activating lymphocytes, comprising:
    a) isolating monocytes from the peripheral blood of a human subject;
    b) mixing the monocytes with 40 ml of culture medium for culturing lymphocytes to obtain a lymphocyte suspension, wherein the complete culture medium for culturing the lymphocytes contains a RPMI 1640 medium supplemented with 200 IU/ml IL-2, 10% of plasma from the human subject and 80 U/ml gentamicin, wherein 40 ml of the lymphocyte suspension contains $5\times10^6$ of the monocytes;
    c) adding the lymphocyte suspension and $5\times10^6$ of the cell ghosts of claim 10 into a T175 culture flask, and
    d) culturing the preparation of step (c) in an incubator containing water-saturated air and 5% $CO_2$ at 37° C.;
    e) adding another 40 ml of complete RPMI 1640 culture medium on Day 4;
    f) transferring cells in the T175 culture flask into a culture bag, adding the complete RPMI 1640 culture medium up to a volume of 400 ml;
    g) adding $8\times10^7$ cell ghosts of claim 10;
    h) transferring the culture obtained in step (g) into two culture bags each containing 640 ml of the complete RPMI 1640 culture medium on Day 10; and
    i) collecting the culture product from each bag to obtain the lymphocytes on Day 12, wherein the lymphocytes are at least one member selected from the group consisting of NK cells, CTL cells and Treg cells.

* * * * *